United States Patent [19]

Zadini et al.

[11] Patent Number: 5,749,856
[45] Date of Patent: May 12, 1998

[54] NEEDLE STICK PROTECTIVE APPARATUS FOR MANUAL CATHETER PLACEMENT DEVICES

[76] Inventors: Filiberto P. Zadini, 16814 Rayen St., North Hills, Calif. 91343; Giorgio C. Zadini, 2237 Hilltop La., Camarillo, Calif. 93012

[21] Appl. No.: 562,524

[22] Filed: Nov. 24, 1995

[51] Int. Cl.$^6$ .................................................. A61M 5/00
[52] U.S. Cl. ........................ 604/162; 604/192; 604/198
[58] Field of Search ................................. 604/162, 164, 604/165, 156, 192, 193, 198

[56] References Cited

U.S. PATENT DOCUMENTS

| | | | |
|---|---|---|---|
| 4,795,443 | 1/1989 | Permenter | 604/198 |
| 5,013,304 | 5/1991 | Russell | 604/164 |
| 5,116,326 | 5/1992 | Schmidt | 604/198 |
| 5,127,905 | 7/1992 | Lemieux | 604/164 |
| 5,215,534 | 6/1993 | De Harde | 604/198 |

*Primary Examiner*—Sam Rimell
*Assistant Examiner*—Luke J. Yeh

[57] ABSTRACT

A needle stick protective apparatus for medical devices having a hollow needle with a sharp tip, a vacuum chamber in flow communication with the hollow needle and a vacuum creating piston-plunger. The apparatus includes an interface member having a rear arm for engaging the piston-plunger and a front portion plate with a needle guard slideable over the needle up to the needle tip to enclose it and to irreversibly lock upon enclosure of the needle tip, shielding the needle tip to provide protection against needle sticks. The sliding of the needle guard over the needle is initiated and sustained, and in certain embodiments is completed, by posterior displacement of the vacuum creating piston-plunger engaged with the arm of the interface member upon blood vessel penetration by the needle. An engagement member converts the rearward displacement of the piston-plunger into a forward displacement of the interface member with the needle guard up to the needle tip. The piston-plunger is manually displaceable to enable a manually driven advancement of the needle guard over the needle upon blood vessel penetration by the needle tip, by acting on the handle of the piston-plunger away and at a safe distance from the needle tip.

10 Claims, 6 Drawing Sheets

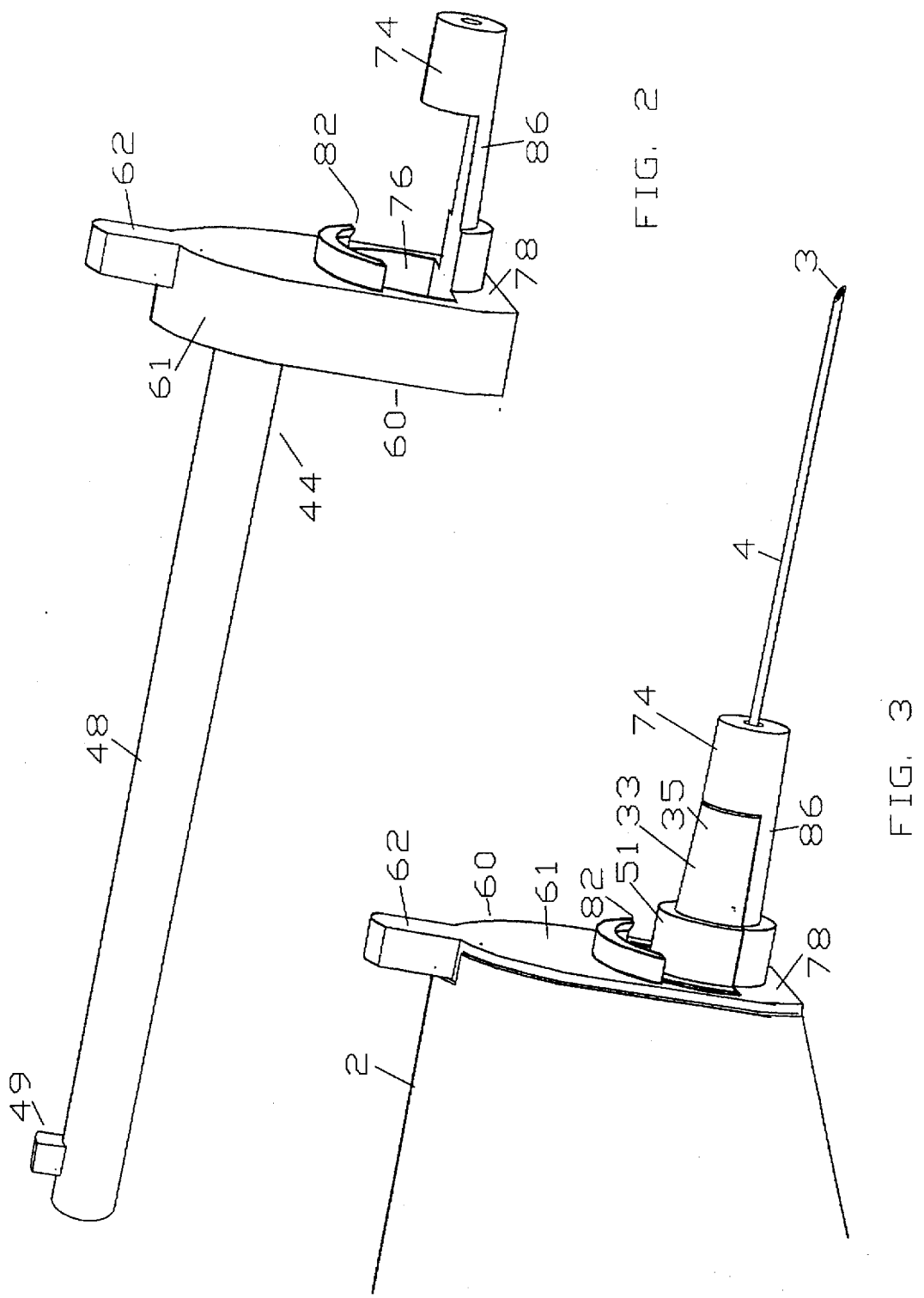

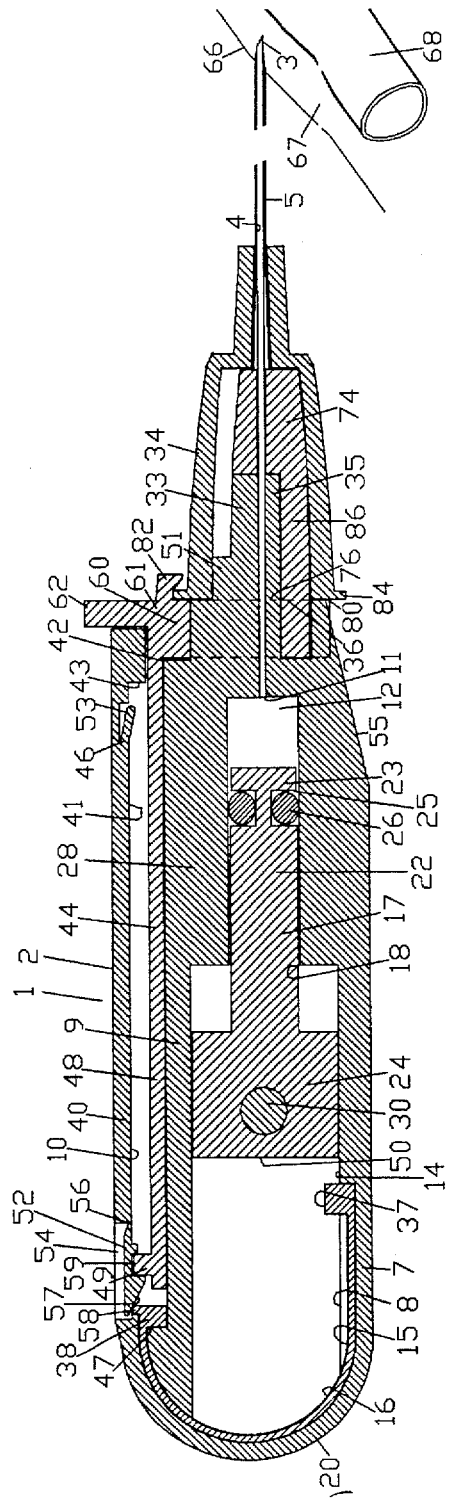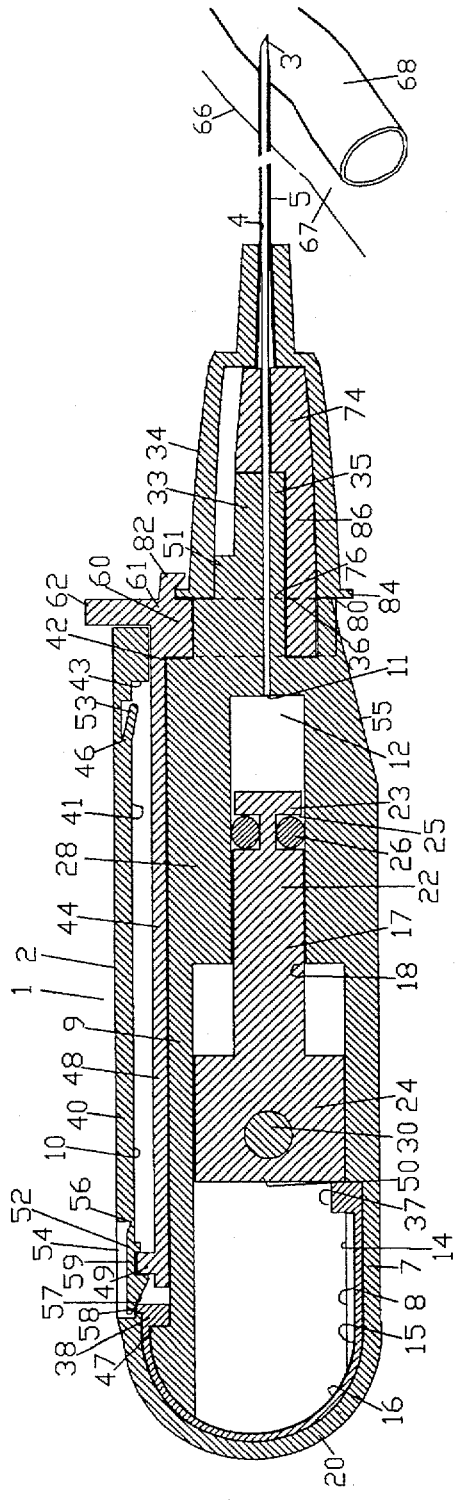

NEEDLE STICK PROTECTIVE APPARATUS FOR MANUAL CATHETER PLACEMENT DEVICES

BACKGROUND OF THE INVENTION

1. Field of the invention

The present invention relates to accidental needle stick protective devices, more specifically to needle sticks protecting devices applicable to the Manual Catheter Placement Device of patent application Ser. No. 08/249,161, filed on May 24, 1194 and now U.S. Pat. No. 5,527,291.

2. Background—Description of Prior Art

Needle sticks among health care workers are not uncommon. Numerous diseases have been proved to be transmitted via needle sticks: hepatitis, malaria, syphilis, AIDS. Risks of transmission are inherent to the medical profession and prevention cannot be achieved only with heightened awareness, education or application of strict guidelines to avoid accidental needle stick punctures. Nothing could be more successful in reducing if not eliminating the risk of transmission of the above mentioned diseases than safe medical devices which prevent contacts of health care workers with contaminated sharps.

A search in the patent office revealed numerous protective devices for the exposed needle tips of hypodermic needles. Two are the basic types of needle sticks protecting devices.

In one type of devices the needle is retracted within a protective shield, manually or by resilient means. In the other group a sleeve or guard is described which is advanced over the needle manually or by resilient means. Locking of the sleeve or guard in respect to the needle and shielding of the needle tip is achieved in either group via various different mechanisms.

However no known protective mechanism has been described for the Manual Catheter Placement Device described in U.S. Pat. No. 5,527,291.

BRIEF SUMMARY OF THE INVENTION

The unique characteristics of the Manual Catheter placement Device described in the above mentioned patent application demand unique solutions for the shielding of the needle tip of the Manual catheter Placement Device.

The Manual Catheter Placement Device is a vascular access device composed of a needle, a catheter concentric with the needle, a housing, means for manually creating vacuum within said housing to accelerate backflow of blood upon occurred blood vessel penetration by the needle tip, means for manually advancing the catheter, said means for manually advancing the catheter being actuated by the means for accelerating backflow of blood.

The Manual Catheter Placement Device permits insertion of the catheter of a catheter-needle assembly into a blood vessel as a smooth continuum process in which penetration of the needle tip into the blood vessel is immediately followed, practically without any pause, by advancement of the catheter into the blood vessel as the means for manually advancing the catheter are actuated by the means for accelerating backflow of blood.

The advantage of the device over the prior art are self-evident: overpenetration and or loss of engagement of the needle tip with the vessel are practically eliminated.

In the embodiments described in the above named patent application, an interface member is interposed between the manual means of accelerating backflow of blood i.e. a displaceable piston, and the catheter. Upon blood vessel penetration by the needle tip, the vacuum creating piston is displaced posteriorly by the operator acting on a handle connected to it. Such posterior displacement of the piston initiates, causes and sustains simultaneous forward displacement of said interface member which in turn carries forward the catheter into the blood vessel.

In the present invention, "Needle Stick Protector for Manual Catheter Placement Devices" the interface member has the dual function of propelling forward the catheter and of shielding the needle tip. Indeed the interface member front portion, interfacing with the catheter hub, is slideable over the needle up to its tip with the purpose of enclosing and shielding it once fully advanced. Shielding of the needle tip is therefore accomplished by advancement of the interface member front portion, such an advancement being initiated and sustained by the posterior displacement of the vacuum creating means occurring upon blood vessel penetration by the needle tip.

Shielding of the needle tip can be accomplished in one step or in two consecutive steps. Indeed the front portion of the interface member accomplishing the dual function of propelling forward the catheter and of shielding the needle tip can be advanced in one single stroke up to the needle tip by a corresponding full posterior displacement of the vacuum creating means, i.e. a piston, or can be accomplished in two steps via manually displacing forward up to the needle tip the front portion of the interface member after its initial advancement caused by the posterior displacement of the piston has stopped.

The needle protection is completed by the locking of the interface member on the Manual Catheter Placement Device upon full advancement of the interface member to a position which permits enclosing, therefore shielding, of the needle tip by the needle guard carried by the front plate of interface member.

OBJECTS OF THE INVENTION

It is an object of the present invention to provide the Manual Catheter Placement Device with a safe and effective method for needle protection.

It is also an object of the present invention to provide the Manual Catheter Placement with a needle protective mechanism which is initiated upon blood vessel penetration by the needle of the manual catheter placement device.

It is also an object of the present invention to provide the Manual Catheter Placement Device with a needle protective mechanism that is simple to operate being actuable with only one hand.

It is an object of the present invention to provide the Manual Catheter Placement Device with a needle protection which does not allow exposure of the needle tip to the environment at any time after tissue penetration.

It is also an object of the present invention to provide the Manual Catheter Placement Device with a needle coverage mechanism that, by not exposing the needle tip after tissue penetration, makes the manual catheter placement device a closed system device, as the blood is not being exposed once the blood vessel has been penetrated.

DRAWING FIGURES

FIG. 1 a side view of the Manual Catheter Placement device at rest prior to use, provided with the needle stick protector.

FIG. 2 is a side view of part of the device of FIG. 1, precisely of the needle protector connected to the interface member.

FIG. 3 is a magnified view of the front portion of the device.

DESCRIPTION OF THE INVENTION

In the form of the present invention chosen for the purpose of illustration, a needle stick protective apparatus for the Manual Catheter Placement Device of patent application Ser. No. 08/249,1610 now issued U.S. Pat. No. 5,527,291 is shown in FIGS. 1, 1A through 1G, 2 and 3.

Figure 1:
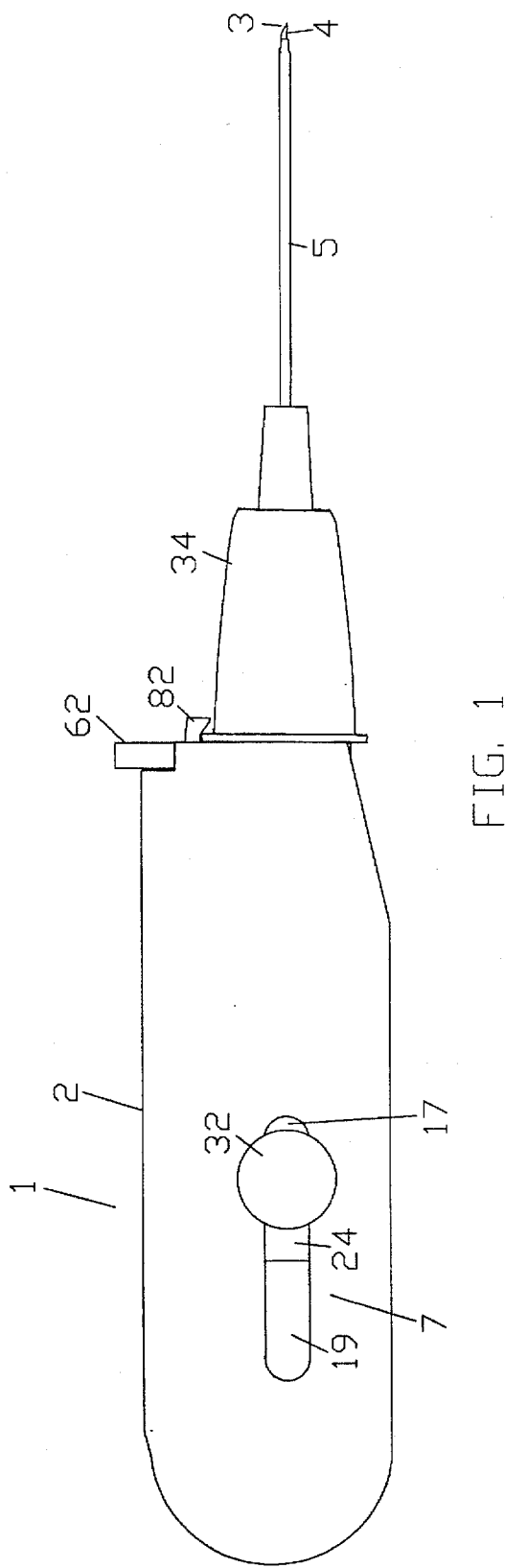
FIG. 1A is across sectional view of the device at rest prior to use.
FIG. 1B is a cross sectional view of the device of FIG. 1 shown in use, armed, after skin penetration by the needle, prior to blood vessel penetration.
FIG. 1C is cross sectional view of the device of FIG. 1 shown in use, at the an early stage of operation, after blood vessel penetration.
FIG. 1D is cross sectional view of the device of FIG. 1 shown in use in a later stage of operation, showing the initial advancement of the interface member with its needle protector propelling the catheter forward.
FIG. 1E is cross sectional view of the device of FIG. 1 shown in use, in a subsequent stage of operation, showing the catheter hub disengaging from the interface member.
FIG. 1F is cross sectional view of the device of FIG. 1 shown in use, in a subsequent stage of operation, showing the needle protector, fully advanced manually by the operator, enclosing the needle tip and locked to the device. The catheter is also shown fully advanced.
FIG. 1G is cross sectional view of the device of FIG. 1 shown in use, in a subsequent stage of operation, showing the manual catheter placement device being withdrawn from the catheter, with the needle protector needle protector enclosing the needle tip and locked to the device.

FIG. 1 is a side view of a Manual Catheter Placement Device with its Needle Stick Protector The device generally indicated at 1, is shown prior to use. The Manual Catheter Placement Device, here illustrated, to which the needle stick protector is applied to it, is basically the same as the device shown in FIG. 1 through 9 of Patent Application Ser. No. 08/249,1610 now issued U.S. Pat. No. 5,527,291. The manual catheter placement device with its needle protector is composed of four main components: a housing 2, a needle 4, a catheter 5 and a needle stick protector 60, partially visible in FIG. 1, but fully visible in FIG. 2, 3 and in cross section in FIG. 1A through 1G.

Figure 1A:
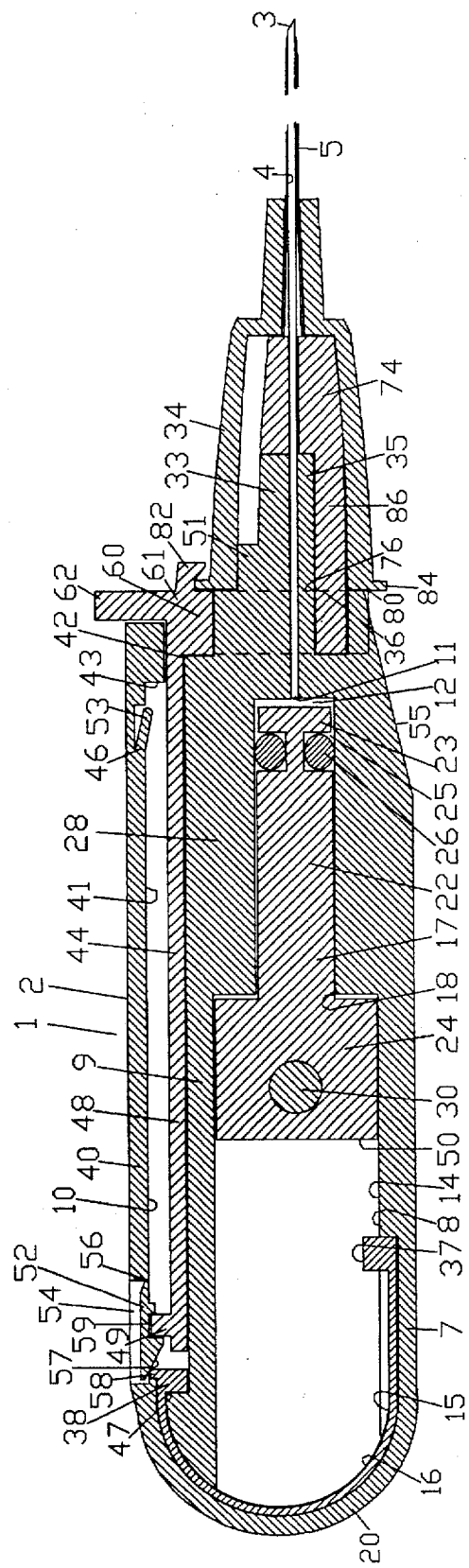

FIG. 1A is a cross-sectional view of the device of FIG. 1 shown at rest. Housing 2 is composed of two parallel chambers of generally cylindrical shape: piston chamber 8 and interface member chamber 10, separated longitudinally by divider wall 9. Piston chamber 8 delimited laterally by sidewall 7, is composed of an anterior or vacuum chamber 12 in communication with hollow needle 4 via opening 11 and posterior chamber 14 of larger diameter than vacuum chamber 12. Piston chamber 8 is closed posteriorly by wall 20. Posterior chamber 14 is in continuity with vacuum chamber 12 via opening 18. Posterior wall 20 is formed with semicircular groove 15 for flexible slideable band or engagements means 16. Flexible slideable band or engagements means 16 is interposed between posterior segment 24 of piston 17, slideably mounted within piston chamber 8, and interface member 44, as it will be apparent from the description below.

Piston, or manually driven vacuum creating means, or blood backflow accelerating means, 17 is composed of two segments: an anterior segment 22, which, prior to use, is in a fully advanced position within chamber 12, and just described posterior piston segment 24 of larger diameter, contained within posterior piston chamber 14. Anterior piston segment 22 has an annular groove 25 formed in proximity of front piston segment 23, where O-ring 26 is mounted in airtight and slideable fashion within side walls 28 of piston chamber 12. Posterior piston segment 24, in continuity with anterior piston segment 22 is slideably mounted in posterior chamber 14. As better seen in FIG. 1, side wall 7 of piston chamber 8 has a lateral slit 19 for arm 30 of side piston handle 32 connected via said arm 30 to posterior piston segment 24 of piston 17. Slit 19 permits the sliding of piston, or vacuum creating means, or blood backflow accelerating means, 17 by the operator acting upon said side piston handle 32.

Piston 17 may also be designed as a piston plunger such as a syringe plunger wherein the operator withdraws the piston by pulling back the plunger. However, the described piston version 17 with side handle 32 is preferable, being designed to render manual withdrawal of piston 17 via displacement of side handle 32 an easy and convenient operation for the operator's hand holding the device, averting the use of two hands, which is likely to occur in the mentioned version with the plunger.

Interface member chamber 10, of generally cylindrical shape, delimited laterally by side wall 40, is open anteriorly via opening 42 while posteriorly receives groove 15 via opening 47. Within groove 15 is slideably mounted, as already described, flexible band or engagement means 16. Flexible band or engagement means 16 is formed with lower end 37 for engagement with posterior aspect 50 of posterior segment 24 of piston 17, and upper end 38 engaging oblique surface 57 of slanted portion of latch 52 as below described. Within chamber 10 is slideably mounted interface member 44. Side wall 40 of interface member chamber 10 is formed posteriorly with window 54 for latch 52, and anteriorly with flexible arrest tab or locking means 53 for the prevention of rearward sliding of the interface member and front arrest, or locking means 43 for the prevention of forward sliding of the interface member.

Latch 52 is pivoted to wall 40 of interface member chamber 10 via flexible pivot 56, and has oblique surface 57 which engages flange 58 of upper end 38 of flexible band 16 and recess 59 which engages arrest tooth 49 of interface member 44. Flexible arrest tab 53 in the anterior portion of intermediate member chamber 10 is pivoted to intermediate member chamber 10 via flexible pivot 46.

Figures 1D, 1E:
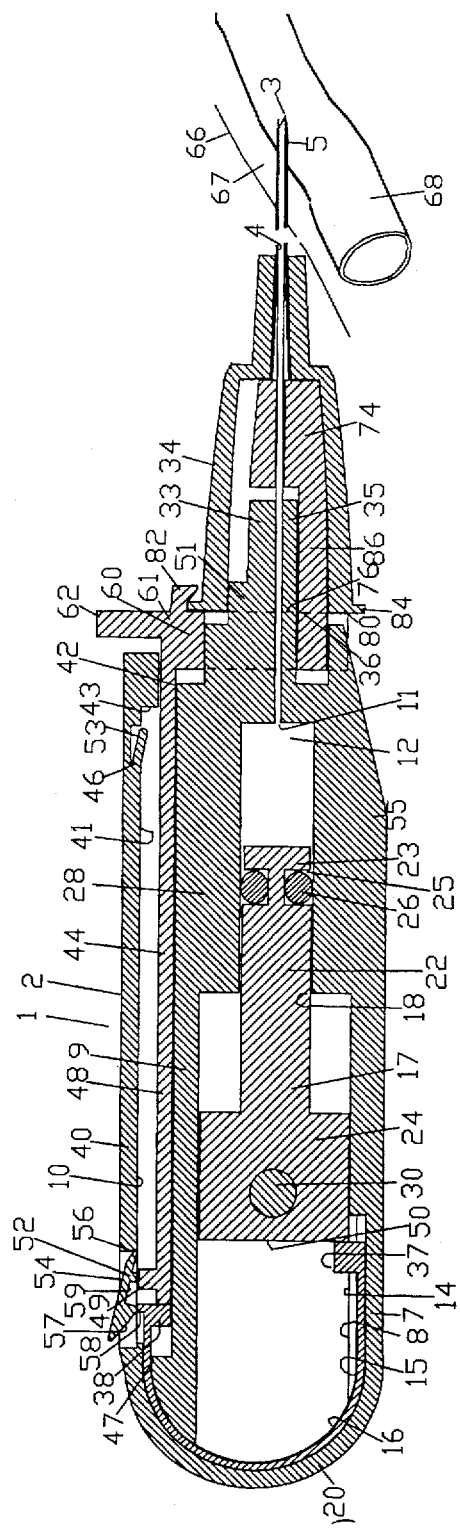

As better shown in FIG. 2, interface member 44 of general cylindrical shape to slideably fit chamber 10, is composed of body segment 48 and front portion or needle protector or catheter propelling member 60. As described above, body 48 of interface member 44 has, at its proximal end, arrest tooth 49, slideable, as shown in FIG. 1B, 1C, 1D, within groove 41 of side wall 40 of intermediate member chamber 10, up to arrest 43. As better shown in FIG. 3, front portion or needle protector 60 of interface member 44 is composed of plate 61 to which is connected, in its antero-inferior segment, needle guard or propelling sleeve 74 via arm or bridge 86. Plate 61 is formed with opening 76 to accommodate needle hub 33, with flat seating 78 adapted to base 80 of catheter hub 34, with semicircularly shaped hook 82 to releasably engage flange 84 of catheter hub 34 and, superiorly, with tab or handle 62. As shown in FIG. 1A and better in FIG. 2, propelling sleeve or guard 74 is of generally truncated conic shape in order to fit within catheter hub 34 in front of needle hub nozzle 35 of needle hub 33.

Needle hub 33 protrudes from anterior end 36 of housing 2. Needle hub 33 has base 51 which precisely fits within catheter hub 34 of catheter 5 and has nozzle 35 in continuity with needle hub base 51 to allow adequate radial leeway for release of catheter hub 34 of catheter 5 from hook 82 of plate 60 of intermediate member 44, when catheter 5 is advanced, as it will be evident in the description of the operation. Housing 2 has a slant 55 in its antero-inferior segment to facilitate the direction of insertion of needle 4 into a vessel lumen.

Hollow needle 4 has tip 3 and protrudes from needle hub 33 as previously described. Catheter 5 and catheter hub 34 are slideably mounted respectively over needle 4 and needle hub 33. Catheter hub 34 has flange 84 releasably engaged with hook 82 of plate 60 with the device at rest prior to use.

DESCRIPTION OF THE OPERATION

The device is operated as follows: as shown in FIG. 1A the operator with the device in his or her hands penetrates the skin 66 of a patient with needle tip 3. The device with its needle is advanced within the subcutaneous tissue 67 toward a presumed location of a blood vessel 68 in an area of expected blood vessel location.

Searching for a vessel may require multiple attempts with frequent repositioning of the needle within the subcutaneous tissue. The searching for the vessel indeed may require partial or full withdrawing of the device with its needle attached to it from the skin and reinserting it into the skin. In case the device needs to be withdrawn during said blood vessel search, catheter 5 will be withdrawn concurrently with the device together with needle 4, remaining firmly connected to the device. Indeed interface member 44 will not be allowed to dislodge from it starting fully retracted position by latch 52 engaging arrest tooth 49 of interface member 44 and it will also retain catheter 5 connected to interface member 44 via hook 82 of plate 61 of interface member 44, said hook 82 engaging flange 84 of catheter 5.

As soon as needle tip 3 is well under skin 66, the operator acts upon handle 32 of piston 17 by sliding it posteriorly through slit 19 of side wall 7 of piston chamber 8. The operator can use any finger of the operating hand. Posterior displacement of piston 17 will create a vacuum in front of anterior piston segment 22 in vacuum chamber 12. However posterior displacement of piston 17 will be of a small amount, being limited by the sealing of needle tip 3 caused the patient tissues, as the operator senses the resistance caused by said vacuum.

As shown in FIG. 1C, as soon as needle tip 3 penetrates blood vessel 68, blood backflows into vacuum chamber 12 in front of anterior piston segment 22 in an accelerated fashion. Piston 17 will be no longer retained in an advanced position due to the vanishing of the vacuum in front of anterior piston segment 22. The operator sensing the fall of resistance to the continuous withdrawing force applied upon piston 17 via said piston handle 32, said fall of resistance occurring upon blood vessel penetration, will displace piston 17 further posteriorly. Piston 17, displaced posteriorly by the operator, will contact band 16 via posterior face 50 of posterior segment 24 of piston 17 engaging lower end 37 of band 16, band 16 being spaced a predetermined amount from posterior face 50 of posterior segment 24 of piston 17.

As shown in FIG. 1D, further posterior displacement of piston 17 on its turn will displace flexible band or engagement means 16 slideable within groove 15. Displacement of band 16, slideable within groove 15 will result in lifting of latch 52 as a result of sliding of flange 58 of upper end 38 of band 16 on oblique surface 57 of slanted portion of latch 52. Lifting of latch 52 will result with dislodging of recess 59 of latch 52 from tooth 49 of interface member 44 and consequent unlocking interface member 44. Further advancement of band 16 will propel forward interface member 44 which in turn will insert catheter 5 forward into vessel 68. During said advancement, hook 82, as shown in FIG. 1D, maintains its engagement with flange b4 of catheter hub 34 and retains catheter 5 firmly attached to the device, not allowing separation of the catheter hub 34 from front portion 60 of the interface member 44 even in case of withdrawal of the device.

Catheter 5 is propelled forward by flat seating 78 of plate 60 adapted to base 80 of catheter hub 34 and by propelling sleeve or needle guard 74. Hook 82 continues to engage with flange 84 of catheter hub 34 for a limited predetermined amount of advancement of interface member 44 while catheter hub 34 slides over base 51 of needle hub 33 due to the fact that base 51 fits exactly within catheter hub 34 in a way to prevent radial leeway and consequent disengagement of flange 84 of catheter hub 5 from hook 82 of plate 61.

As shown in FIG. 1E, when catheter hub 34 is furtherly advanced over nozzle 35 of needle hub 33, adequate radial leeway is allowed for catheter hub 34 to disengage from hook 82 of plate 61, permitting disengagement of catheter 5 from propelling sleeve or needle guard 74. Interface member advancement by band 16 will cease as soon as piston 17 is fully displaced posteriorly by the operator. Further advancement of interface member 44 will complete the forward sliding motion of interface member 44 initiated by vacuum creating means 17, and is accomplished with the purpose of enclosing needle tip 3 with needle guard 74. In this embodiment further advancement of interface member 44 is carried out by manually advancing interface member 44 by acting upon tab 62.

Figure 1F:
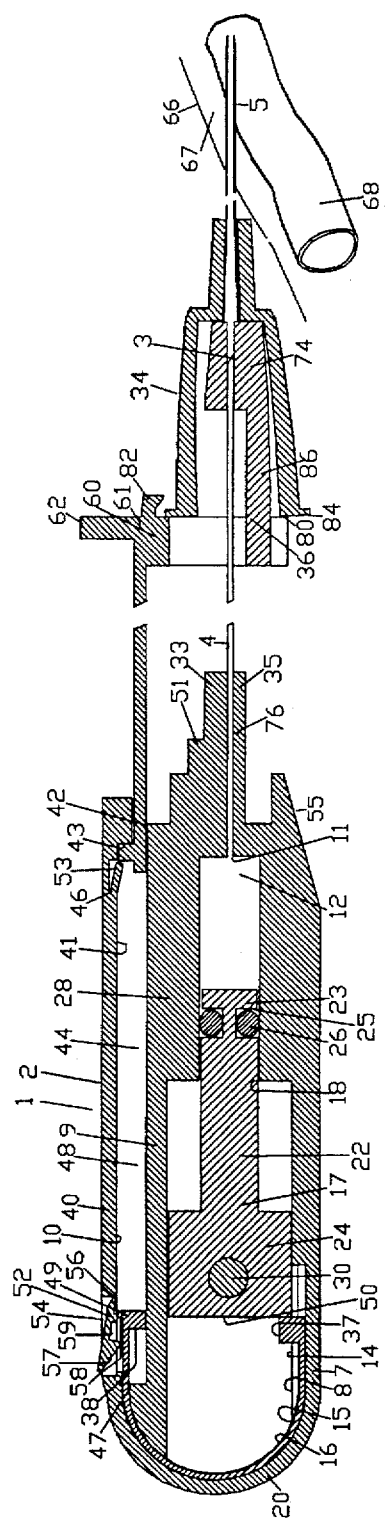

FIG. 1F shows the needle protector, fully advanced manually by the operator, enclosing the needle tip and locked to the device. The catheter is also shown fully advanced.

Figure 1G:
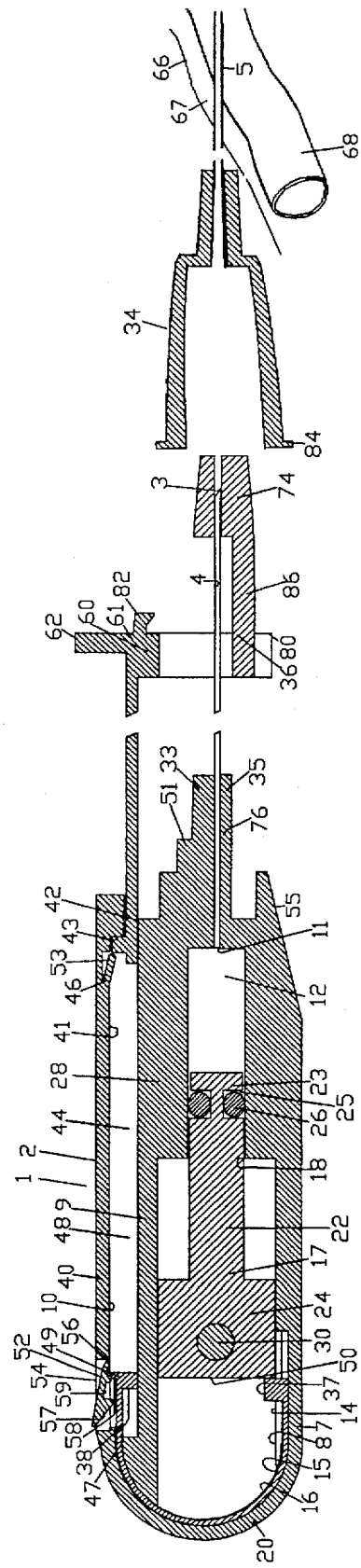

FIG. 1G shows the manual catheter placement device being withdrawn from the catheter, with the needle protector needle protector enclosing the needle tip and locked to the device.

Arrest and locking of propelling sleeve or needle guard 74 in advanced position beyond needle tip 3 for the purpose of needle tip shielding is achieved by the fact that interface member 44 will not be allowed to move in either direction, neither forward nor backward, respectively by arrest 43 and locking means 53 engaging tooth 49.

Indeed engagement of arrest tooth 49 of interface member 1044 with front arrest 43 will not permit further forward advancement of intermediate member 44 or eventual exit of interface member 44 from interface member chamber 10 while flexible tab or locking means 53 will not permit posterior displacement of interface 44 in respect to housing 2.

The enclosing of needle tip by the propelling sleeve or needle guard 74 of the interface member 44 for the purpose of protection from needle sticks is therefore, in the embodiment described, manually accomplished by manual forward sliding of interface member by the operator pushing forward tab or handle 62 of plate 60 of interface member 44, after the initial advancement of catheter 5 by interface member 44 to a predetermined length, in response to vanishing of the vacuum as described above.

In another embodiment, not illustrated, interface member 44 can be fully advanced in a single step by the presence a longer flexible band associated with an elongated backward riding of the piston. Band 16 can indeed be construed of such a length so as to permit full advancement of interface member 44 in one single stroke up to the needle tip 3. Needle tip 3 will be thus enclosed by needle guard or propelling sleeve 74 upon advancement of interface member 44, said advancement being not only initiated but also sustained from beginning to end by rearward displacement of piston or vacuum means 17. In such embodiments no second manual step is thus required to complete the advancement of needle protector 60. Locking of interface member in a fully advanced position is achieved exactly in the same manner as in the embodiments previously described.

After the initial manual predetermined advancement, which is enabled by the vacuum creating means in response to the vanishing of the vacuum, is completed, further advancement of needle protector 60 connected to interface member 44, can also be accomplished by resilient means such as a spring, which can propel needle protector 60 further forward, up to needle tip 3 of needle 4 with the purpose of enclosing it.

Obviously, numerous other variations and modifications can be made without departing from the spirit of the present invention. Therefore, it should be clearly understood that the forms of the present invention described above and shown in the figures of the accompanying drawings are illustrative only and are not intended to limit the scope of the present invention.

What we claim is:

1. A needle stick protector comprising:

a hollow needle having a tip;

a vacuum chamber in flow communication with the hollow needle;

means for creating a vacuum within the vacuum chamber, an interface member, engaged with said means for creating vacuum, said interface member having a front portion slideable over the needle, wherein said front portion of the interface member slideable over the needle is also adapted to enclose the tip of said needle upon full forward advancement of said interface member, said forward advancement being initiated by said means for creating vacuum, an engaging means for converting a rearward displacement of said vacuum creating means into a forward displacement of said interface member, said means for creating vacuum being manually displaceable upon blood vessel penetration by said needle to enable a manually driven advancement of said interface member;

said interface member being irreversibly lockable in its advanced position by locking means to provide a needle stick protection with said front portion of said interface member.

2. The device of claim 1 wherein said interface member is advanceable to a full forward position by said means for creating said vacuum so as to enclose said needle tip with said front portion of said interface member.

3. The device of claim 1 wherein said interface member comprises handle means so as to be manually advanceable to a full forward position, so as to enclose said needle tip with said front portion of said interface member, after being advanced of a predetermined amount by said means for creating said vacuum.

4. The device of claim 1 wherein said interface member is advanceable to a full forward position by resilient means, so as to enclose said needle tip with said front portion of said interface member, after being advanced of a predetermined amount by said means for creating said vacuum.

5. The device of claim 1 wherein said interface member front portion comprises a needle guard of generally hollow cylindrical shape concentric to the needle, said needle guard having an inner diameter comparable to the outer diameter of the needle, said inner diameter of said needle guard being sufficiently greater than the outer diameter of the needle to allow sliding of said guard over said needle up to a forward arrest position, said needle guard being of sufficient length to entirely enclose the needle tip and to extend further anteriorly beyond the needle tip in its forward arrest position.

6. The device of claim 1 wherein said interface member front portion comprises a protective sleeve of generally cylindrical shape concentric to the needle, said protective sleeve having an inner diameter comparable to the outer diameter of the needle, said inner diameter of said protective sleeve being sufficiently greater than the outer diameter of the needle to allow sliding of said protective guard over the needle up to a forward arrest position, said protective sleeve being of sufficient length to entirely enclose the needle tip and to extend further anteriorly beyond the needle tip in its forward arrest position.

7. A needle stick protector comprising:

a hollow needle having a tip;

means for accelerating backflow of blood upon blood vessel penetration by said needle, an interface member engaged with said means for accelerating backflow of blood, said interface member having a front portion slideable over the needle, wherein said front portion of the interface member slideable over the needle is also adapted to enclose the tip of said needle upon full forward advancement of said interface member, said forward advancement being initiated by said means for accelerating backflow of blood, an engaging means for converting a rearward displacement of said means for accelerating backflow of blood into a forward displacement of said interface member, said means for accelerating backflow of blood being manually displaceable upon said blood vessel penetration to enable a manually driven advancement of said interface member;

said interface member being irreversibly lockable in its advanced position by locking means to provide a needle stick protection with said front portion of said interface member.

8. The device of claim 1 further comprising a vascular catheter over the needle, said front portion of said interface member slideable over the needle engaging said catheter to advance said catheter upon advancement of said interface member.

9. A needle stick protection apparatus for medical devices having a hollow needle with a sharp tip, a vacuum chamber in flow communication with the hollow needle and a vacuum creating member within the vacuum chamber, comprising:

a vacuum creating member a needle an interface member having a front portion slideable over the needle, said front portion of the interface member being adapted to enclose the tip of said needle upon full forward displacement of said interface member, and engaging means for converting a rearward displacement of said vacuum creating member into a forward displacement of said interface member, said forward displacement of said interface member being initiated by said member for creating vacuum, said member for creating vacuum being manually displaceable upon blood vessel penetration by said needle to enable a manually driven advancement of said interface member, said interface member being irreversibly lockable in its advanced position by locking means to provide a needle stick protection with said front portion of said interface member.

10. The device of claim 9 further comprising a vascular catheter over the needle, said front portion of said interface member slideable over the needle engaging said catheter to advance said catheter upon forward displacement of said interface member.

* * * * *